(12) United States Patent
Atkinson

(10) Patent No.: US 8,603,523 B2
(45) Date of Patent: Dec. 10, 2013

(54) PHARMACEUTICAL COMPOSITION AND ITS USE IN A METHOD FOR TREATMENT OF PATIENTS WITH UPPER RESPIRATORY MUCOSAL CONGESTION

(75) Inventor: Hartley Atkinson, Auckland (NZ)

(73) Assignee: Aft Pharmaceuticals Limited, Takapuna, Auckland (NZ)

( * ) Notice: Subject to any disclaimer, the term of this patent is extended or adjusted under 35 U.S.C. 154(b) by 887 days.

(21) Appl. No.: 11/922,271

(22) PCT Filed: Jun. 17, 2005

(86) PCT No.: PCT/NZ2005/000132
§ 371 (c)(1),
(2), (4) Date: Feb. 17, 2009

(87) PCT Pub. No.: WO2006/135254
PCT Pub. Date: Dec. 21, 2006

(65) Prior Publication Data
US 2009/0215811 A1    Aug. 27, 2009

(51) Int. Cl.
*A61K 9/20* (2006.01)
*A61K 31/137* (2006.01)
*C07D 221/06* (2006.01)

(52) U.S. Cl.
USPC .............................. 424/464; 514/649; 546/93

(58) Field of Classification Search
None
See application file for complete search history.

(56) References Cited

U.S. PATENT DOCUMENTS

| 4,282,233 | A | * | 8/1981 | Vilani | 514/290 |
| 5,541,210 | A |   | 7/1996 | Cupps et al. | |
| 6,132,758 | A | * | 10/2000 | Munayyer et al. | 424/439 |
| 2006/0127473 | A1 | * | 6/2006 | Nichols | 424/464 |

FOREIGN PATENT DOCUMENTS

| RU | 2220740 A | 1/2004 |
| WO | WO-98/18470 A | 5/1998 |
| WO | WO-01/89527 A | 11/2001 |
| WO | WO-03/089007 A1 | 10/2003 |
| WO | WO-2004/023984 A2 | 3/2004 |

OTHER PUBLICATIONS

CAS (STN) Registry No. 79794-75-5 (Nov. 16, 1984).*
Sodium metabisulfite. Remington: The Science and Practice of Pharmacy. 19th Edition (vol. II) 1995, p. 1382.*
CAS Registry No. 79794-75-5 (Nov. 16, 1984).*
Boner, A.L. et al.; Efficacy and Safety of Loratadine Suspension in the Treatment of Children With Allergic Rhinitis; Allergy, 1989, 44, 437-441.
Lutsky, GN, et al.; A Comparative Study of the Efficacy and Safety of Loratadine Syrup and Terfenadine Suspension in the Treatment of 3- to 6- Year-Old Children with Seasonal Allergic Rhinitis; PubMed; Clin Ther. Sep.-Oct. 1993; 15(5):855-65.

* cited by examiner

*Primary Examiner* — Daniel Sullivan
*Assistant Examiner* — Peter Anthopolos
(74) *Attorney, Agent, or Firm* — Edwards Wildman Palmer LLP; Jeffrey D. Hsi

(57) ABSTRACT

The present invention relates to a pharmaceutical composition including loratidine, its use in the treatment of upper respiratory mucosal congestion and a method of administration of the composition. Particularly, though not exclusively, the invention relates to a pharmaceutical composition including loratidine in an amount suitable for administration a maximum of 4 times a day, and a second active that is a hydroxyl-$\alpha$-[(methylamino)methyl]-benzenemethanol, such 3-hydroxyl-$\alpha$-[(methylamino) methyl]-benzenemethanol (phenylephrine), or salt thereof.

20 Claims, No Drawings

PHARMACEUTICAL COMPOSITION AND ITS USE IN A METHOD FOR TREATMENT OF PATIENTS WITH UPPER RESPIRATORY MUCOSAL CONGESTION

CROSS-REFERENCE TO RELATED APPLICATIONS

This application is the U.S. national phase under 35 U.S.C. section 371 of PCT International Application No. PCT/NZ2005/000132, filed Jun. 17, 2005, the contents of which are incorporated herein by reference in their entirety.

INTRODUCTION

The present invention relates to a pharmaceutical composition including loratidine, its use in the treatment of upper respiratory mucosal congestion and a method of administration of the composition. Particularly, though not exclusively, the invention relates to a pharmaceutical composition including loratidine in an amount suitable for administration a maximum of 4 times a day, and a second active that is a hydroxyl-α-[(methylamino)methyl]-benzenemethanol, such 3-hydroxyl-α-[(methylamino) methyl]-benzenemethanol (phenylephrine), or salt thereof.

BACKGROUND

Upper respiratory mucosal congestion caused by infections such as the common cold and influenza, or allergic rhinitis, can lead to a number of nasal and ocular symptoms. These include rhinitis and sinusitis, nasal and sinus congestion or excessive secretions, headaches, sneezing and itching and excessive lacrimation. Infections such as the common cold can be very common over the winter months, while the symptoms of rhinitis are also common in some parts of the world.

Such symptoms can be treated with antihistamine containing products and with decongestant containing products. The products are generally sold as part of non-prescribed medicines which are available to patients through outlets such as pharmacies.

There are a number of antihistamine actives available including non-sedating antihistamines such as loratadine, cetirizine or fexofenadine. These products provide less sedation in comparison to normal antihistamines, and therefore more readily allow a user to perform tasks such as driving or operating machinery.

Fexofenadine is an active carboxylic acid metabolite of terfenadine. The latter has been withdrawn due to serious cardiotoxic reactions and drug interactions. In depth information regarding the risk of these reactions is not available for fexofenadine. But according to the AHFS Drug Information 2004 as a result of comparative studies between fexofenadine and terfenadine, it is thought that the clinical efficacy of terfenadine is attributable to fexofenadine.

The risk of similar reactions to terfenadine being created by the use of fexofenadine has not been ruled out.

Cetirizine is another non-sedating antihistamine. However, in comparison to loratadine, cetirizine has been reported to have a higher incidence of adverse drug reactions (ADRs), especially central nervous system ADRs[1]. Some studies have also indicated that cetirizine has a higher incidence of somnolence than loratadine.

Loratadine is disclosed in U.S. Pat. No. 4,282,233 as a non-sedating antihistamine useful as an anti-allergy agent in, for example, the treatment of seasonal allergic rhinitis symptoms such as sneezing and itching. Loratadine has a maximum over the counter (OTC) dose of 10 mg per day. It is generally administered once a day at the maximum dose for a number of reasons including perceived efficacy and patient compliance. However, there are adverse effects that can occur at peak concentration and also with end-of-dose diminution of effect.

There are also a number of decongestant agents available. Phenylephrine has in the past been used as a decongestant agent. However, its use has now been surpassed by the next generation of decongestant products including pseudoephedrine. Pseudoephedrine tends to act with a higher efficacy and has a slightly longer half-life than previous generation products such as phenylephrine, providing an increase in the efficiency for relieving symptoms.

Combination antihistamine and decongestant products are available as a result of a demand for combination products that meet the problems associated with multiple product ingestion. Combinations of loratadine and new generation decongestants such as pseudoephedrine have been disclosed with a view to administering the combination once or twice a day. Disclosure of such combinations has been made in WO 98/18470 to Schering Corporation for example.

Combinations of the older style decongestant drugs, such as phenylephrine, and sedating antihistamines are available in liquid preparations. The use of such products has however been superseded by use of combinations using the newer style decongestant drugs, such as pseudoephedrine, for the reasons mentioned above.

There are several solid dose products currently available which combine the newer style drugs, such as pseudoephedrine, together with non-sedating antihistamine. Examples of those available in Australasia are given in Table 1 below.

TABLE 1

Current Combination Non-Sedating Antihistamine and Nasal Decongestant Solid Dose Form Products Available in Australasia

| Product | Decongestant | Non-sedating Antihistamine | Daily Dose |
| --- | --- | --- | --- |
| Clarinase 12 Hour | Pseudoephedrine 240 mg | Loratadine 5 mg | 1 tablet twice daily |
| Clarinase 24 Hour Relief | Pseudoephedrine 240 mg | Loratadine 10 mg | 1 tablet daily |
| Demazin Non-Drowsy | Pseudoephedrine 240 mg | Loratadine 5 mg | 1 tablet twice daily |
| Telfast Decongestant | Pseudoephedrine 240 mg | Fexofenadine 60 mg | 1 tablet twice daily |
| Zyrtec Decongestant | Pseudoephedrine 240 mg | Cetirizine 5 mg | 1 tablet twice daily |

However, products containing pseudoephedrine are now subject to abuse problems associated with illicit drug use in the community. The pseudoephedrine component of these medications can be converted to potent stimulants such as methamphetamine and methcathinone both of which are CNS stimulants with great potential for habituation and physical and/or psychic dependence. This has resulted in pharmacy hold-ups, stolen stock from warehouses and significant related crime. The resulting crime, and its effects on the outlets which supply these medications to the market, means that some outlets are choosing not to stock these products, or at least restrict their availability. This makes them less accessible to those with a genuine need for the medications. In the United States, for example, legislation restricts the threshold content of pseudoephedrine OTC ("over the counter") products, for example, can contain no more than 3 g of pseudoephedrine (in terms of the base) packaged in packs of 1 or 2 dosage units per pack or as package size liquid preparations.

It would be beneficial to have an alternative medication capable of being available without a prescription which is effective in treating the symptoms of upper respiratory mucosal congestion and which mitigates at least some of the problems identified above.

Other objects of the invention may become apparent from the following description, which is given by way of example only.

SUMMARY OF THE INVENTION

In a first aspect the invention provides a method of treating upper respiratory mucosal congestion by administering to a patient in need thereof a pharmaceutical composition including about 2.5 mg loratadine or a suitable salt thereof four times a day.

Preferably the composition is administered qid.

Preferably the pharmaceutical composition further includes a hydroxy-$\alpha$-[(methylamino) methyl]-benzenemethanol, most preferably 3-hydroxy-$\alpha$-[(methylamino) methyl]-benzenemethanol (phenylephrine), or a suitable salt thereof.

Preferably the pharmaceutical composition includes about 8 to 10 mg of phenylephrine free base or a corresponding amount in the form of a suitable salt thereof.

Preferably the phenylephrine salt is the hydrochloride salt.

Preferably the pharmaceutical composition is in a solid dosage form.

In one embodiment the present invention provides a method of treating upper respiratory mucosal congestion using a pharmaceutical composition which includes about 8 to 10 mg phenylephrine free base or a corresponding amount in the form of a suitable salt thereof, and about 2.5 mg loratadine or a corresponding amount in the form of suitable salt thereof, wherein the patient is administered the composition four times a day.

Preferably the composition is administered qid.

Preferably the phenylephrine salt is the hydrochloride salt. More preferably the composition includes 10 to 12.2 mg of the hydrochloride salt.

Preferably the method includes the administration of a pill, capsule or tablet containing about 8 to 10 mg phenylephrine and about 2.5 mg loratadine, or corresponding amounts in the form of suitable salts thereof, 4 times a day.

In another aspect the present invention provides the use of about 8 to 10 mg phenylephrine and about 2.5 mg loratadine, or corresponding amounts in the form of suitable salts thereof, in the manufacture of a medicament for administration to a patient 4 times a day for the treatment of upper respiratory mucosal congestion.

Preferably the medicament is manufactured for administration qid.

Preferably the phenylephrine is in a salt form, more preferably as the hydrochloride salt.

In another aspect this invention provides a pharmaceutical composition for the treatment of upper respiratory mucosal congestion containing phenylephrine, or a suitable salt thereof, and loratadine, or a suitable salt thereof, wherein the phenylephrine is present in an amount of about 8 to 10 mg and the loratadine is present in an amount of about 2.5 mg.

Preferably the phenylephrine salt is the hydrochloride salt.

Preferably the pharmaceutical composition includes pharmaceutically acceptable non-active excipients and/or carriers.

Preferably the pharmaceutical composition is a pill, capsule or tablet.

In one embodiment the pharmaceutical composition is 10.00 mg phenylephrine hydrochloride, 2.50 mg loratadine, 180.40 mg lactose, 140.00 mg maize starch, 10.365 mg pregelatinised starch, 0.20 mg lake of quinoline yellow, 0.40 mg sodium metabisulphite, 0.14 mg disodium EDTA, 3.00 mg talc, and 3.00 mg magnesium stearate In another aspect the invention provides a pack including pills, tablets or capsules containing a pharmaceutical composition including phenylephrine and loratadine, wherein the phenylephrine is present in an amount of about 10 mg and the loratadine is present in an amount of about 2.5 mg wherein the pack includes instructions to administer the composition a maximum of 4 times a day.

Preferably the phenylephrine is in a salt form, more preferably as the hydrochloride salt.

Preferably the 4 times a day administration is qid.

Preferably the pack is a blister pack.

In another aspect the invention provides a container containing a syrup including loratadine and phenylephrine, or suitable salts thereof, at concentrations suitable for administration of about 2.5 mg loratadine and about 8 to 10 mg phenylephrine per unit dose, the bottle including instructions to administer an amount of syrup that will deliver about 2.5 mg loratadine and about 8 to 10 mg phenylephrine per unit dose 4 times a day.

Preferably the phenylephrine is in a salt form, more preferably as the hydrochloride salt.

In alternative aspects the invention provides the use of about 2.5 mg loratadine in the manufacture of a medicament for the treatment of upper respiratory/mucosal congestion; wherein preferably the medicament is for administration a maximum of four times a day.

Preferably the use further includes the use of 8 to 10 mg of a suitable phenylephrine, preferably a corresponding amount in the form of a suitable salt, in the manufacture of the medicament.

In another aspect the invention provides a pharmaceutical composition for use in the treatment of upper respiratory mucosal congestion, the composition including 2.5 mg of loratadine, together with pharmaceutically acceptable carriers and/or excipients.

Reference to "treatment of upper respiratory mucosal congestion" is intended to include treatment of symptoms of upper mucosal respiratory congestion such as rhinitis, sinusitis, nasal and sinus congestion, excessive secretions, headaches, sneezing, itching and/or excessive lacrimation. Treatment is intended to be read in terms of alleviate or mitigate, rather than cure.

Where the phrase "corresponding amount" is used in respect of the amount of a suitable salt, the amount of the salt required to provide the equivalent dose of the free base is intended, e.g. 12.2 mg of phenylephrine hydrochloride is the amount corresponding to 10 mg of phenylephrine as the free base.

DETAILED DESCRIPTION OF A PREFERRED EMBODIMENT

The invention in general terms provides a method of treating upper respiratory mucosal congestion using a pharmaceutical composition which includes loratadine in amounts suitable for administration 4 times a day. The composition additionally includes a decongestant.

Furthermore the inventor has recognized that the selection of a decongestant that is a hydroxyl-$\alpha$-[(methylamino)

methyl]-benzenemethanol, or salt thereof, does not result in the disadvantages that accrue from the selection of a decongestant that is a α-[1-(methylamino) ethyl]-benzenemethanol.

The lower efficacy and shorter half life of the selected decongestant can be offset, at least to a limited extent, by its use in combination with loratadine. The advantages of this particular combination have not before been recognized for the compositions disclosed in the specifications accompanying international application no. PCT/IB03/01197 (Publication no. WO 03/089007) or international application no. PCT/US2003/029095 (Publication no. WO 2004/023984).

The composition contains loratadine (a non-sedating antihistamine), and preferably phenylephrine (a decongestant). The pharmaceutical composition is safe to be supplied on a non-prescription basis and can therefore be purchased over the counter ("OTC").

TABLE 2

Dose Rates of Phenylephrine and Pseudoephedrine

| Agent | Dose | Reference |
|---|---|---|
| Phenylephrine | 10 mg 3-4 times a day | Martindale 28th edition |
|  | 10 mg q 4 hours | Drug Tx, 4th edition |
| Pseudoephedrine | 60 mg 3-4 times a day | Martindale 28th edition |
|  | 60 mg qid or 120 mg bd | Drug Tx, 4th edition |

As stated in the Martindale reference a number of suitable phenylephrine salts can be used.

The phenylephrine component can be delivered as any suitable salt form (eg HCl, tartrate). The base form could also be used. Suitable salts will be well known to the skilled person. Reference herein to the use of phenylephrine is intended to include reference to delivery as a suitable salt.

Loratadine has a maximum OTC daily administration of 10 mg per day. As for phenylephrine, suitable salts could also be used to deliver the loratadine as would be known to the skilled person. Reference herein to loratadine is intended to include administration as a suitable salt.

Surprisingly the use of about 2.5 mg loratadine administered 4 times daily (eg qid) has therapeutic advantages over the usual 10 mg administered once a day. It is hypothesised that this may be due to the ideal concentration-time profile for continuous effect being a constant concentration over time (as would occur with a continuous infusion). As the 2.5 mg loratadine use flattens out the differences between peak and trough concentrations in the plasma, this administration regime most closely resembles the effect of a continuous infusion. The flatter concentration-time profile provides advantages of fewer peak concentration adverse effects, and less end-of-dose diminution of effect. Administration of the composition, in terms of loratadine effect, provides distinct advantages to the user. This effect forms the basis of one aspect of the invention.

While the use of a combination of a non-sedating antihistamine and a decongestant is known for the treatment of upper mucosal respiratory congestion, this currently involves the latest generation of decongestant medications and ordinarily involves the use of maximum OTC doses of the actives in a single administration. Phenylephrine, an earlier generation medication, has a different potency to pseudoephedrine on a milligram by milligram basis. The development of decongestants such as pseudoephedrine, which provide more efficient means of decongestion, means that the older generation of decongestants, like phenylephrine are not actives that would ordinarily be included in combination medications. The development of a loratadine plus phenylephrine product which allows the therapeutic and use advantages of the present invention is therefore unexpected and is a significant advance.

The inventor has recognized that the use of an older generation drug (phenylephrine) while less efficient would, in combination with an effective non-sedating antihistamine, still provide a helpful medication to alleviate the symptoms of upper mucosal respiratory congestion.

Administration of the combination including phenylephrine (preferably in a suitable salt form eg hydrochloride, tartrate) 4 times a day (eg qid preferably) provides therapeutic and use advantages that mitigate the therapeutic effect of using the older style drug while offering additional advantages. This enables an alternative medication to be accessible to symptom sufferers, without restraints being placed on the availability of this medication due to social issues resulting from the use of the newer style drugs. In using such an older generation medicament in combination with a non-sedating antihistamine the inventor has also recognized the importance of minimizing the potential for adverse drug reactions.

The administration of the phenylephrine 4 times a day allows peak effects of this drug to be delivered quarterly over the day thus mitigating the fast half-life effect of phenylephrine on decongestant efficacy. It is the combination of the preferably quarterly administration of the loratadine and the phenylephrine and the interaction of effect between them, that allows this pharmaceutical composition to provide the user with such a useful alternative to combinations that use new style decongestant drugs. Optionally, the phenylephrine could be included such that it is released slowly from the composition but it is not considered that this is necessary. It may be that the combined effect of the two drugs when administered 4 times per day could be termed synergistic from this perspective. It is the combination of the beneficial effects stemming from the preferably quarterly administration of both drugs that allows the user to receive benefits over and above those provided by simply administering the drugs individually or in combination to meet the maximum daily dose once or twice per day. Administration for treatment of severe symptoms is 4 times daily and as close to qid as possible. This is to maximize the advantages gained from the flat peak/trough concentrations of the loratadine in the plasma. This allows the composition to provide a useful alternative to existing compositions that use new generation decongestants from an efficacy perspective, and provides a composition that does not suffer from the social problems that hinder use of the new generation decongestants (eg pseudoephedrine). This combination effect (loratadine and phenylephrine) forms the basis of another, or additional, aspect of the invention.

The 2.5 mg or 2.5 mg/10 mg qid regimen does have disadvantages over the other regimens in terms of drug compliance. Once daily and twice daily regimens are superior to qid regimens in terms of compliance. However compliance is also related to the severity of symptoms, and patients are ordinarily reminded to be compliant if their symptoms persist. In this case, non compliance when symptoms have diminished is not likely to be a disadvantage. While once or twice daily administration may have compliance advantages, the beneficial effect of the 2.5 mg loratadine 4 times a day (eg qid) to treat severe upper respiratory mucosal congestion symptoms individually or together with phenylephrine is still significant.

The pharmaceutical combination according to the invention allows for the delivery of a total of around 10 mg loratadine and 40 mg phenylephrine per day, administered in 4 doses. The pharmaceutical composition will include loratadine in an amount of about 2.5 mg and phenylephrine (preferably as the hydrochloride salt) in an amount of about 10 mg. The amount of actives used in the composition will of course be within the margins of error allowed for pharmaceutical use.

The compositions also include non-active components such as binders and other excipients as would be known by a person skilled in the art. The ingredients can be formulated into a tablet, pill or capsule using known pharmaceutical carriers and excipients (such as diluents, binders, colorants, antioxidants, chelating agents, gledants and/or lubricants). The composition is formulated into a tablet of a size capable of containing the amounts of ingredient preferred. Preferably the composition is manufactured using pharmaceutically acceptable ingredients as would be known to the skilled person, such as maize or pre-gelatinised starch, lactose (eg monohydrate) microcrystalline cellulose, magnesium stearate, quinoline yellow, sodium metabisulphite, EDTA, talc.

Purified water will preferably be used. As will be appreciated by persons skilled in the art, purified water may be used during the formulation process, which includes a drying process. The drying process evaporates the water from the composition, meaning that the water does not contribute to the final weight of the composition.

The tablets/pills will preferably be presented to the consumer as part of a pharmaceutical pack, such as a blister pack, as will be well known. The pack should have an even number of pills contained within it and have instructions about the maximum number of pills/tablets to be taken at any one time and within a set timeframe. In the present case, one tablet/pill/capsule should be taken 4 times per day (preferably qid). It is of course possible that the pills/tablets/capsules could be sold contained in a bottle, the pills held loosely within that bottle. Again, instructions on administration 4 times daily (preferably qid) would be included.

In a further alternate embodiment the pharmaceutical composition can be a syrup for administration to children, and patients with difficulty swallowing pills. Standard methods for the production of such syrups are well known in the art. The syrup would be contained in a bottle, vial or like container and prepared in a manner capable of delivering about 2.5 mg loratadine, and preferably about 10 mg phenylephrine per dose, 4 times daily. This would be achievable by producing a syrup having a specified concentration of the actives, in conjunction with instructions about how much of the syrup should be taken per quarterly dose. With regard to doses for younger children it will be recognized that lower doses of such a syrup are appropriate. In respect of loratadine the dose for children under 12 years should be less than 5 mg/day.

The invention can therefore be seen to be a method of treating upper respiratory mucosal congestion in a patient in need thereof using a pharmaceutical composition including about 2.5 mg loratadine and preferably about 10 mg phenylephrine, that is administered to a patient 4 times a day. The pharmaceutical composition itself is also the subject of the invention as is the use of about 2.5 loratadine and preferably about 10 mg phenylephrine in the manufacture of a medicament for such treatment.

A preferred composition is shown in Table 3 below.

EXAMPLE

The components shown in Table 3 are combined into a single tablet and taken by either adults or children aged 12 years or older. The tablet may be taken up to 4 times a day giving a maximum dose of 10 mg of loratadine and 40 mg of phenylephrine per day.

TABLE 3

Combination Composition Formulation

| Name of ingredient | Qty. per tablet | | Function | Reference to specifications |
|---|---|---|---|---|
| Active ingredient: | | | | |
| Phenylephrine Hydrochloride | 10.00 | mg | Active ingredient | Ph. Eur. |
| Loratadine | 2.50 | mg | Active ingredient | IHS |
| Other ingredients: | | | | |
| Lactose | 180.40 | mg | Diluent | Ph. Eur. |
| Maize starch | 140.00 | mg | Diluent, Binder | Ph. Eur. |
| Pregelatinised starch | 10.365 | mg | Binder | Ph. Eur. |
| Lake of quinoline yellow | 0.20 | mg | Colourant | IHS |
| Sodium metabisulphite | 0.40 | mg | Antioxidant | Ph. Eur. |
| Disodium EDTA | 0.14 | mg | Chelating Agent | Ph. Eur. |
| Talc | 3.00 | mg | Glidant | Ph. Eur. |
| Magnesium stearate | 3.00 | mg | Lubricant | Ph. Eur. |

The formulation administered 4 times daily provides effective 24 hour treatment of the symptoms of upper respiratory mucosal congestion with reduced adverse effects and without using pseudoephedrine as the decongestant.

Where in the foregoing description there has been made reference to specific components or integers of the invention having known equivalents then such equivalents are herein incorporated as is individually set forth.

Although this invention has been described by way of example only and with reference to possible embodiments thereof it is to be understood that modifications or improvements may be made without departing from the scope or spirit of the invention as defined in the attached claims.

REFERENCES (1) The American Society of Health System Pharmacists Drug Information 2004. G. K. McEvoy (Editor), Bethesda, USA

The invention claimed is:

1. A pharmaceutical composition comprising:
   8-10 mg of the decongestant phenylephrine or a pharmaceutically-equivalent amount in the form of a pharmaceutically-acceptable salt thereof; and
   2.5 mg of the antihistamine loratadine or a pharmaceutically-equivalent amount in the form of a pharmaceutically-acceptable salt thereof; and
   wherein the pharmaceutical composition is solid; and
   wherein the pharmaceutical composition is in the form of a unit dose selected from the group consisting of a pill, a capsule, and a tablet.

2. The pharmaceutical composition of claim 1, further comprising sodium metabisulphite.

3. The pharmaceutical composition of claim 1, further comprising a compound selected from the group consisting of ethylenediaminetetraacetic acid (EDTA) and disodium ethylenediaminetetraacetate (disodium EDTA).

4. The pharmaceutical composition of claim 2, further comprising a compound selected from the group consisting of ethylenediaminetetraacetic acid (EDTA) and disodium ethylenediaminetetraacetate (disodium EDTA).

5. The pharmaceutical composition of claim 1, comprising 8 mg of phenylephrine.

6. The pharmaceutical composition of claim 1, comprising 10 mg of phenylephrine.

7. The pharmaceutical composition of claim 5, further comprising sodium metabisulphite.

8. The pharmaceutical composition of claim 5, further comprising a compound selected from the group consisting of ethylenediaminetetraacetic acid (EDTA) and disodium ethylenediaminetetraacetate (disodium EDTA).

9. The pharmaceutical composition of claim 7, further comprising a compound selected from the group consisting of ethylenediaminetetraacetic acid (EDTA) and disodium ethylenediaminetetraacetate (disodium EDTA).

10. The pharmaceutical composition of claim 6, further comprising sodium metabisulphite.

11. The pharmaceutical composition of claim 6, further comprising a compound selected from the group consisting of ethylenediaminetetraacetic acid (EDTA) and disodium ethylenediaminetetraacetate (disodium EDTA).

12. The pharmaceutical composition of claim 10, further comprising a compound selected from the group consisting of ethylenediaminetetraacetic acid (EDTA) and disodium ethylenediaminetetraacetate (disodium EDTA).

13. The pharmaceutical composition of claim 1, comprising a pharmaceutically-equivalent amount of the following pharmaceutically-acceptable phenylephrine salt: phenylephrine hydrochloride.

14. A pharmaceutical composition comprising:
   10-12.2 mg of the decongestant phenylephrine hydrochloride; and
   2.5 mg of the antihistamine loratadine or a pharmaceutically-equivalent amount in the form of a pharmaceutically-acceptable salt thereof;
   wherein the pharmaceutical composition is solid; and
   wherein the pharmaceutical composition is in the form of a unit dose selected from the group consisting of a pill, a capsule, and a tablet.

15. The pharmaceutical composition of claim 14, comprising 10 mg of phenylephrine hydrochloride.

16. The pharmaceutical composition of claim 14, comprising 12.2 mg of phenylephrine hydrochloride.

17. The pharmaceutical composition of claim 14, comprising 2.5 mg of loratadine.

18. The pharmaceutical composition of claim 17, comprising 10 mg of phenylephrine hydrochloride.

19. The pharmaceutical composition of claim 17, comprising 12.2 mg of phenylephrine hydrochloride.

20. A tablet comprising:
   10.00 mg phenylephrine hydrochloride;
   2.50 mg loratadine;
   180.40 mg lactose;
   140.00 mg maize starch;
   10.365 mg pre-gelatinised starch;
   0.20 mg lake of quinoline yellow;
   0.40 mg sodium metabisulphite;
   0.14 mg disodium EDTA;
   3.00 mg talc; and
   3.00 mg magnesium stearate.

* * * * *